(12) United States Patent
Breindel et al.

(10) Patent No.: US 11,446,467 B2
(45) Date of Patent: Sep. 20, 2022

(54) OVERMOLDED SEPTUM FOR CATHETER HUB

(71) Applicant: Smiths Medical ASD, Inc., Plymouth, MN (US)

(72) Inventors: Jay T. Breindel, Branford, CT (US); Kathryn Felicito, Cheshire, CT (US); Harsh D. Chheda, Cheshire, CT (US); James Edward Abitabilo, Bristol, CT (US); James Muskatello, Southington, CT (US); Christopher Roehl, New Hartford, CT (US)

(73) Assignee: Smiths Medical ASD, Inc., Plymouth, MN (US)

( * ) Notice: Subject to any disclaimer, the term of this patent is extended or adjusted under 35 U.S.C. 154(b) by 217 days.

(21) Appl. No.: 16/580,849

(22) Filed: Sep. 24, 2019

(65) Prior Publication Data

US 2020/0094016 A1   Mar. 26, 2020

Related U.S. Application Data

(60) Provisional application No. 62/736,266, filed on Sep. 25, 2018.

(51) Int. Cl.
| | | |
|---|---|---|
| B29C 45/14 | (2006.01) | |
| A61M 25/00 | (2006.01) | |
| B29L 31/00 | (2006.01) | |

(52) U.S. Cl.
CPC .... *A61M 25/0014* (2013.01); *A61M 25/0097* (2013.01); *B29C 45/14336* (2013.01); *B29L 2031/7542* (2013.01)

(58) Field of Classification Search
CPC .......... A61M 25/0014; A61M 25/0097; A61M 2039/0036; B29C 45/00
See application file for complete search history.

(56) References Cited

U.S. PATENT DOCUMENTS 3,470,604 A * 10/1969 Zenick .................. B29C 66/131
29/447
3,720,210 A * 3/1973 Diettrich ................ A61B 17/34
604/533

(Continued)

FOREIGN PATENT DOCUMENTS

JP       2008-532663 A    8/2008
KR    10-2003-0065561 A    8/2003

(Continued)

OTHER PUBLICATIONS

Search Report dated Jan. 23, 2020 for Application No. PCT/US2019/052613, 11 pages.

*Primary Examiner* — Matthew J Daniels
*Assistant Examiner* — Andrew D Graham
(74) *Attorney, Agent, or Firm* — Patterson Thuente Pedersen, P.A.

(57) ABSTRACT

A method of constructing a catheter assembly having an integrated septum. The method comprising molding a catheter hub having a distal end, a proximal end, and an internal wall defining an internal fluid passageway therebetween, the internal fluid wall defining an injection mold window located between the distal end and the proximal end; seating a catheter tube within the internal fluid passageway of the catheter hub, such that a proximal end of the catheter tube resides within the internal fluid passageway of the catheter hub, and a distal end of the catheter tube extends distally from the distal end of the catheter hub; plugging at least a proximal end of the catheter hub with a mold core shut off pin; and injection molding a septum in at least a portion of the internal fluid passageway between the mold core shut off pin and the proximal end of the catheter tube through the injection mold window.

15 Claims, 7 Drawing Sheets

(56) References Cited

U.S. PATENT DOCUMENTS

| | | | | |
|---|---|---|---|---|
| 4,523,968 A * | 6/1985 | McCool | A61M 25/0014 | 156/198 |
| 4,755,649 A * | 7/1988 | Barker | B29C 66/12821 | 219/765 |
| 4,802,947 A * | 2/1989 | Bartholomew | A61M 25/0014 | 156/380.5 |
| 4,846,809 A * | 7/1989 | Sims | A61M 5/326 | 604/198 |
| 4,964,854 A * | 10/1990 | Luther | A61M 5/3273 | 604/166.01 |
| 5,322,518 A * | 6/1994 | Schneider | A61M 39/24 | 604/167.03 |
| 5,403,291 A * | 4/1995 | Abrahamson | A61M 25/007 | 600/435 |
| 5,480,380 A * | 1/1996 | Martin | A61M 5/1582 | 604/284 |
| 5,510,065 A * | 4/1996 | McFarlane | B29C 45/14598 | 264/313 |
| 5,713,849 A * | 2/1998 | Bosma | A61M 1/85 | 604/28 |
| 5,749,857 A * | 5/1998 | Cuppy | A61M 25/0606 | 604/161 |
| 5,800,399 A * | 9/1998 | Bogert | A61M 25/0014 | 604/164.11 |
| 5,800,410 A * | 9/1998 | Gawreluk | A61M 25/0014 | 604/524 |
| 5,810,869 A * | 9/1998 | Kaplan | A61M 25/0014 | 604/96.01 |
| 6,192,568 B1 * | 2/2001 | Kafrawy | A61M 25/0009 | 264/157 |
| 6,616,630 B1 * | 9/2003 | Woehr | A61M 5/3273 | 604/110 |
| 6,837,873 B1 * | 1/2005 | Polley | A61M 25/0009 | 604/160 |
| 7,670,317 B2 * | 3/2010 | Cindrich | A61M 39/0606 | 604/167.01 |
| 7,799,400 B2 * | 9/2010 | Zihlmann | B29C 45/16 | 604/524 |
| RE45,896 E * | 2/2016 | Stout | A61M 25/0606 | |
| 11,071,849 B2 * | 7/2021 | Ng | A61M 25/0606 | |
| 2002/0120231 A1 * | 8/2002 | Douglas | A61M 39/1011 | 604/82 |
| 2003/0088213 A1 * | 5/2003 | Schweikert | A61M 25/0097 | 604/177 |
| 2004/0034333 A1 * | 2/2004 | Seese | A61M 1/285 | 604/523 |
| 2004/0097903 A1 * | 5/2004 | Raulerson | A61M 1/3661 | 604/523 |
| 2004/0167478 A1 * | 8/2004 | Mooney | A61B 17/3417 | 604/264 |
| 2004/0243103 A1 * | 12/2004 | King | A61M 25/0097 | 604/533 |
| 2005/0033237 A1 * | 2/2005 | Fentress | B29C 45/16 | 604/165.03 |
| 2005/0040557 A1 * | 2/2005 | Flynn | A61M 25/0026 | 264/248 |
| 2005/0059958 A1 * | 3/2005 | Lessard | A61M 25/0009 | 604/533 |
| 2005/0070878 A1 * | 3/2005 | Triplett | A61M 25/0028 | 604/523 |
| 2005/0080398 A1 * | 4/2005 | Markel | A61M 1/3661 | 604/508 |
| 2005/0234499 A1 * | 10/2005 | Olson | A61M 25/1036 | 606/192 |
| 2006/0264821 A1 * | 11/2006 | Vo | A61M 25/0015 | 604/95.05 |
| 2007/0196414 A1 * | 8/2007 | Hammarsten | A61M 25/0606 | 424/422 |
| 2007/0260221 A1 * | 11/2007 | Chesnin | A61M 25/0097 | 604/523 |
| 2008/0009832 A1 * | 1/2008 | Barron | A61M 25/0097 | 604/533 |
| 2008/0097344 A1 * | 4/2008 | McKinnon | A61M 25/0618 | 604/263 |
| 2008/0214991 A1 * | 9/2008 | Haarala | A61M 25/0026 | 604/43 |
| 2008/0294145 A1 * | 11/2008 | Eddings | A61M 25/0097 | 604/533 |
| 2009/0005741 A1 * | 1/2009 | Martin | A61M 25/0074 | 604/256 |
| 2009/0069792 A1 * | 3/2009 | Frey | A61M 25/0026 | 604/535 |
| 2009/0093794 A1 * | 4/2009 | Holtz | B29C 66/81429 | 604/523 |
| 2009/0157052 A1 * | 6/2009 | Verbitsky | B29C 45/14467 | 604/533 |
| 2010/0102490 A1 * | 4/2010 | Smith | A61M 5/158 | 264/537 |
| 2010/0130939 A1 * | 5/2010 | Voss | A61M 25/0017 | 604/167.03 |
| 2010/0204648 A1 * | 8/2010 | Stout | A61M 25/0606 | 604/122 |
| 2012/0004622 A1 * | 1/2012 | Leeflang | A61M 39/0606 | 604/246 |
| 2012/0150130 A1 * | 6/2012 | Triel | A61M 25/001 | 604/264 |
| 2012/0296290 A1 * | 11/2012 | Argauer | A61M 25/0014 | 604/272 |
| 2013/0053826 A1 * | 2/2013 | Shevgoor | A61M 25/0015 | 604/523 |
| 2013/0090608 A1 * | 4/2013 | Stout | A61M 39/00 | 604/256 |
| 2013/0218082 A1 * | 8/2013 | Hyer | A61M 25/0097 | 604/167.06 |
| 2014/0074028 A1 * | 3/2014 | Sonderegger | A61M 25/001 | 604/151 |
| 2014/0128820 A1 * | 5/2014 | Braga | A61M 39/284 | 604/284 |
| 2014/0180261 A1 * | 6/2014 | Nyman | A61L 29/085 | 604/544 |
| 2014/0249487 A1 * | 9/2014 | Lynn | A61M 39/045 | 604/256 |
| 2014/0306383 A1 * | 10/2014 | Harding | B29C 45/14 | 264/478 |
| 2015/0051583 A1 * | 2/2015 | Horvath | A61M 25/0015 | 604/508 |
| 2015/0157827 A1 * | 6/2015 | Glasel | A61M 25/0026 | 604/284 |
| 2015/0190612 A1 * | 7/2015 | Schaffner | A61M 39/10 | 604/533 |
| 2015/0219255 A1 * | 8/2015 | Reuter | B65D 47/06 | 222/545 |
| 2015/0306368 A1 * | 10/2015 | Lin | A61M 25/0606 | 604/265 |
| 2016/0008569 A1 * | 1/2016 | Harding | A61M 25/0097 | 604/256 |
| 2016/0008570 A1 * | 1/2016 | Glozman | A61M 5/1418 | 604/544 |
| 2016/0220791 A1 * | 8/2016 | Akcay | A61B 5/15003 | |
| 2016/0220805 A1 * | 8/2016 | Goral | A61M 21/02 | |
| 2017/0119997 A1 * | 5/2017 | Burkholz | A61M 25/008 | |
| 2017/0151417 A1 * | 6/2017 | Takemura | B29C 45/72 | |
| 2017/0239443 A1 * | 8/2017 | Abitabilo | A61M 25/0625 | |
| 2018/0093085 A1 * | 4/2018 | Burkholz | A61M 25/0606 | |
| 2018/0161540 A1 * | 6/2018 | Fantuzzi | A61M 25/0014 | |
| 2019/0022367 A1 * | 1/2019 | Burkholz | A61M 25/0606 | |
| 2019/0321616 A1 * | 10/2019 | Akahori | A61M 39/10 | |
| 2020/0009366 A1 | 1/2020 | Abitabilo et al. | | |

FOREIGN PATENT DOCUMENTS

| | | |
|---|---|---|
| WO | WO 02/051494 A1 | 7/2002 |
| WO | WO 2019/152630 A1 | 8/2019 |

* cited by examiner

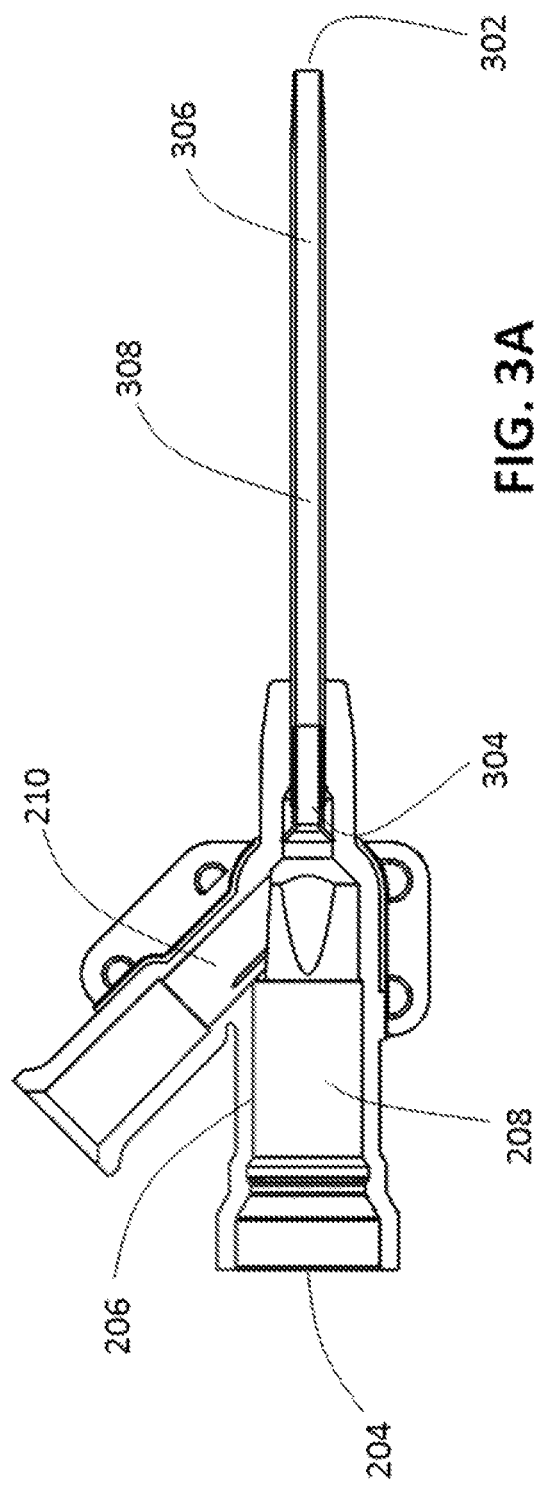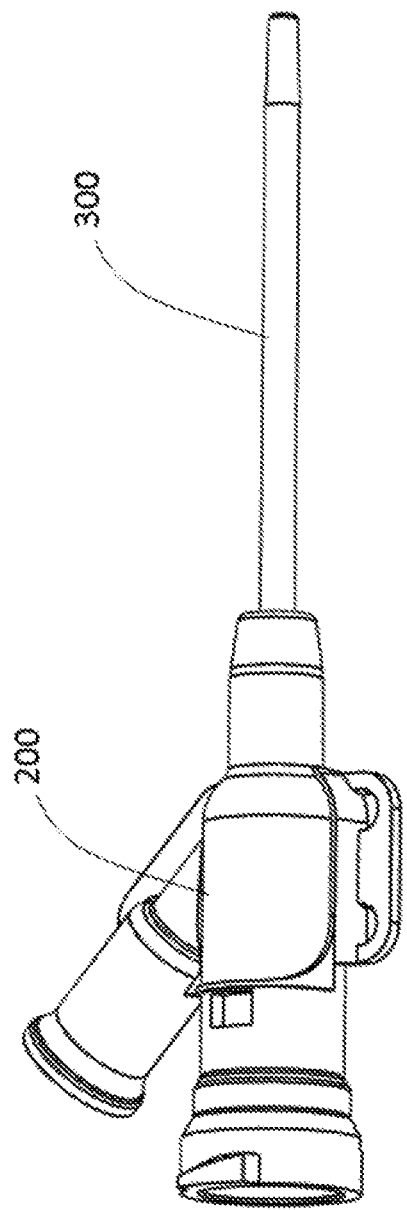

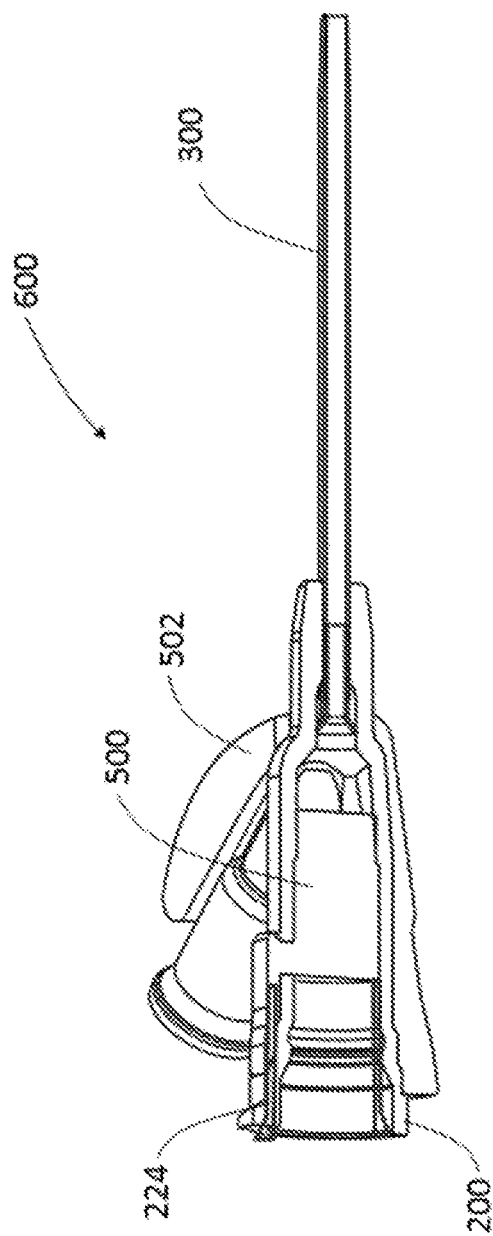
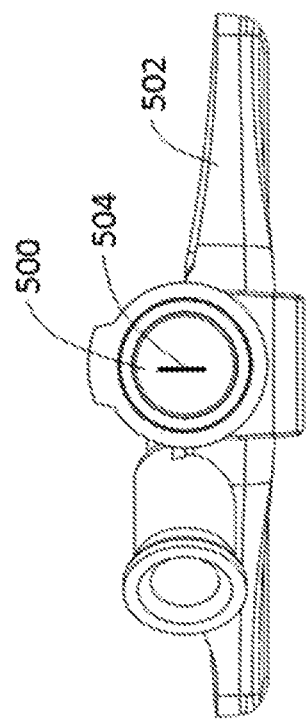
FIG. 5A
FIG. 5B

OVERMOLDED SEPTUM FOR CATHETER HUB

RELATED APPLICATION

The present application claims the benefit of U.S. Provisional Application No. 62/736,266 filed Sep. 25, 2018, which is hereby incorporated herein in its entirety by reference.

TECHNICAL FIELD

The present disclosure relates generally to intravenous catheters, and more particularly to closed system intravenous catheter assemblies having an improved catheter design and method of production.

BACKGROUND

Intravenous (IV) therapy is a versatile technique used for the administration of medical fluids to and withdrawal of bodily fluids from patients. IV therapy has been used for various purposes, such as the maintenance of blood and electrolyte balance, the transfusion of blood, the administration of nutritional supplements, chemotherapy, and the administration of drugs and medications. These fluids, collectively referred to herein as medicaments, may be administered intravenously by injection through a hypodermic needle, or intermittently or continuously by infusion using a needle or catheter. A common intravenous access device utilized by clinicians is the Peripheral Intravenous Catheter (PIVC).

A PIVC is made of a soft, flexible plastic or silicone, generally between fourteen to twenty-four gauge in size. In the conventional venipuncture procedure, a catheter is inserted into a vein in the patient's hand, foot, or the inner aspect of the arm or any vein in the body that will accept an IV catheter. Typically PIVCs are "over the needle" catheters, where a catheter is coaxially placed over an introducer needle of an intravenous catheter insertion device. In order to properly place the catheter into the patient's vein, the introducer needle is used to puncture the skin, tissue, and vein wall to provide a path for placement of the catheter into the vein.

Placement of the catheter generally includes preparation of a biological site of the patient. Often a tourniquet is applied proximal to the biological site and a variety of techniques can be used to dilate the patient's vein. While wearing disposable gloves, the clinician cleanses the biological site and a vein is retracted or anchored by placing a thumb over the vein about fifty to seventy five mm distal to the site. The introducer needle and catheter are introduced into the vein by inserting a beveled sharpened tip of the introducer needle into the vein at about a twenty to thirty degree angle, with the bevel facing up in order to pierce one wall of the vein. The catheter thus rides with the introducer needle through the skin, tissue, and vein wall into the patient's vein. To finish placement, the introducer needle and catheter are lowered towards the skin to decrease the entry angle, and the catheter is advanced slightly into the vein. Once the catheter is satisfactorily positioned within the vein, the introducer needle is typically withdrawn from inside the catheter, and the connection between the catheter and the intravenous catheter device is loosened, so that the catheter can be advanced further into the vein as desired. The catheter can then be secured in place on the biological site by adhesive tape, while the intravenous catheter insertion device is properly disposed of in a sharps container.

In some cases, the PIVC defines a side port operably connectable to an IV fluid supply or other medical device, often via a pre-attached extension tube having a Luer lock connector positioned some distance away from the insertion site, thereby promoting ease-of-use and minimizing patient discomfort. Such catheters are often referred to as "closed system" catheters, as they typically include a septum that seals the needle path after the introducer needle has been withdrawn from the catheter, thereby inhibiting blood or bodily fluid from the patient from escaping from the catheter to the ambient environment, and reducing the risk of exposure of blood or other bodily fluids to clinicians, particularly a consideration of sensitivity were blood borne disease may be present. With such catheters, it is common that the septum is breached a single time (i.e., with the passage of the insertion needle therethrough). After withdrawal of the insertion needle, the septum closes, thereby permanently sealing a proximal end of the catheter hub such that the flow of fluid through the catheter is directed through the side port. Over the years, various efforts have been made to simplify the construction of closed system catheters, with the goal of reducing overall production costs. For example, U.S. Pat. Publ. Nos. 2016/0220805 and 2017/0239443, the disclosures of which are hereby incorporated herein by reference in their entirety, disclose a number of catheter hub designs configured to improve functionality, while reducing production costs. Nevertheless, there is an ever present need to further streamline manufacturing and reduce production costs. The present disclosure addresses these concerns.

SUMMARY OF THE DISCLOSURE

Embodiments of the present disclosure provide an improved design and method of production configured to reduce cost and assembly time of a closed system catheter. In particular, embodiments of the present disclosure eliminate the adding of a septum to catheter assembly as a separate, stand-alone component; rather, the catheter hub is specifically adapted to enable the septum to be injection molded directly into a partially assembled catheter assembly. Molding a septum into the catheter hub alleviates a manufacturer of the burden of intricately positioning a separate, stand-alone within the catheter hub during construction, as molding a septum into the catheter hub ensures that the septum is properly positioned. Molding a septum into the catheter hub also enables the septum to be shaped and sized to reduce voids or pockets within an internal fluid passageway of the catheter hub where slower moving fluid flowing therethrough may tend to stagnate.

One embodiment of the present disclosure provides a method of constructing a catheter assembly having an integrated septum, including: holding a catheter hub having a distal end, a proximal end, and an internal wall defining an internal fluid passageway therebetween, the internal wall defining an injection mold window located between the distal end in the proximal end; seating a catheter tube within the internal fluid passageway of the catheter hub, such that a proximal end of the catheter tube resides within the internal fluid passageway of the catheter hub, and a distal end of the catheter tube extends distally from the distal end of the catheter hub; plugging at least the proximal end of the catheter hub with the mold core shutoff pin; and injection molding a septum in at least a portion of the internal fluid passageway between the mold core shutoff pin and the proximal end of the catheter tube through the injection mold window.

In one embodiment, the method further comprises defining a slit and/or pierce in the septum. In one embodiment, the method further comprises adding a proximal hub component to the proximal end of the catheter hub to actually compress the septum. In one embodiment, the method further comprises overmolding wings around at least a portion of the catheter hub concurrently with the molding of the septum. In one embodiment, the internal wall of the catheter hub further defines a side port in communication with the internal fluid passageway. In one embodiment, the method further comprises operably coupling a length of tubing to the side port. In one embodiment, the septum extends at least partially through the injection mold window, thereby eating in the retention of the septum within the internal fluid passageway.

Another embodiment of the present disclosure provides a method of constructing a catheter assembly having an integrated septum, including loading a catheter tube having a proximal end and a distal end into a catheter assembly mold; overmolding a catheter hub around at least the proximal end of the catheter tube, the catheter hub having a distal end, a proximal end, and an internal wall defining an internal fluid passageway therebetween, the internal wall defining an injection mold window located between the distal end in the proximal end; plugging at least the proximal end of the catheter hub with the mold core shutoff pin; and injection molding a septum in at least a portion of the internal fluid passageway between the mold core shutoff pin and the proximal end of the catheter tube through the injection mold window.

Another embodiment of the present disclosure provides a catheter assembly having an integrated septum. The catheter assembly can include a catheter hub, a catheter tube, and a septum. The catheter hub can have a distal end, a proximal end, and an internal wall defining an internal fluid passageway therebetween. The internal wall can further define an injection mold window located between the distal end in the proximal end. The catheter tube can be positioned within the catheter hub, such that a proximal end of the catheter tube resides within the internal fluid passageway of the catheter hub, and a distal end of the catheter tube extends distally from the distal end of the catheter hub. The septum can fill at least a portion of the internal fluid passageway between the proximal end of the catheter hub and a proximal end of the catheter tube, the septum can extend at least partially through the injection mold window.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 3A is a cross-sectional view depicting a catheter tube positioned within a catheter hub, in accordance with an embodiment of the disclosure.

FIG. 3B is a perspective view depicting the catheter tube and catheter hub of FIG. 3A.

FIG. 5A is a cross-sectional view depicting a catheter assembly, in accordance with an embodiment of the disclosure.

FIG. 5B is a profile view depicting the catheter assembly of FIG. 5A.

Figure 1:
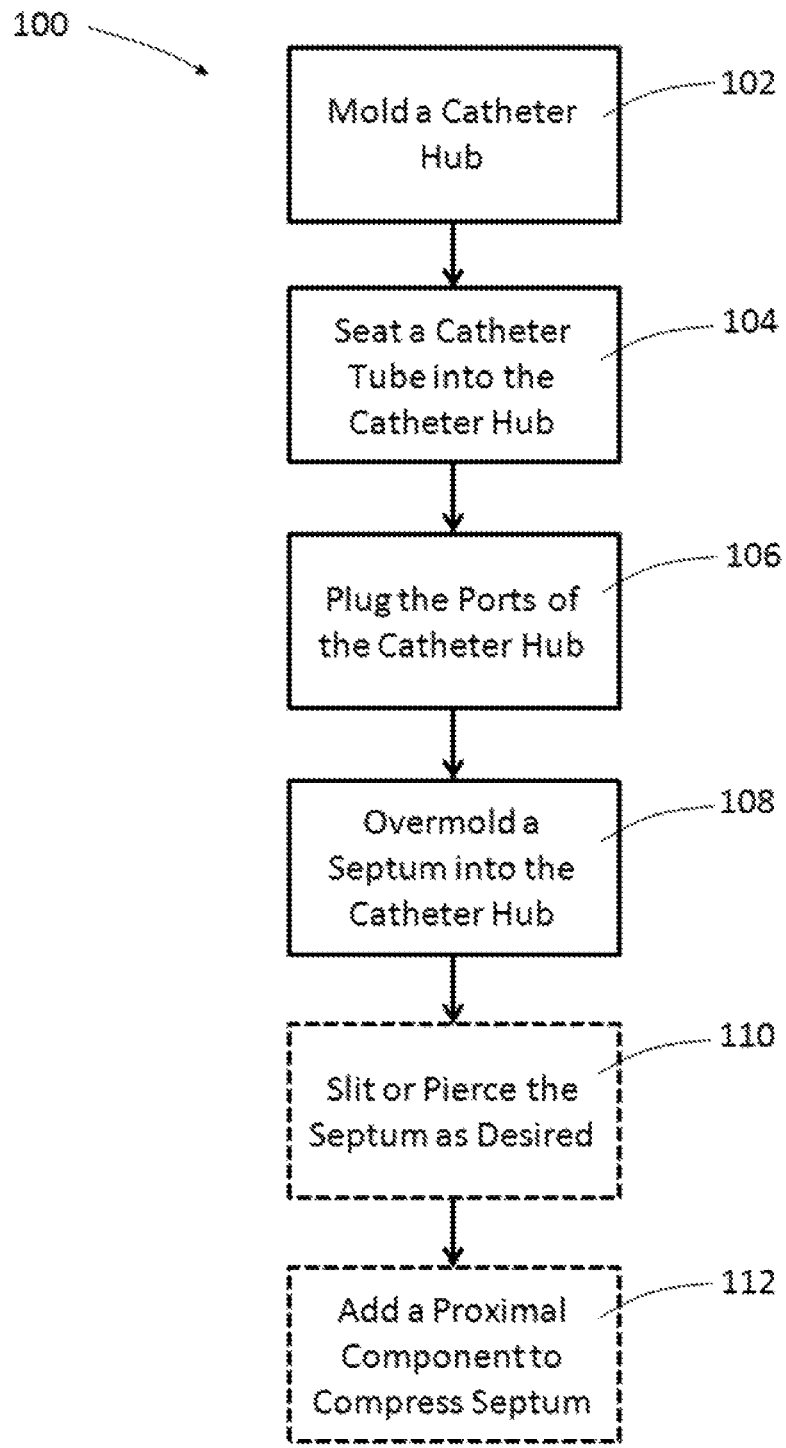
FIG. 1 is a flowchart depicting a process of constructing a catheter assembly, in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 2:
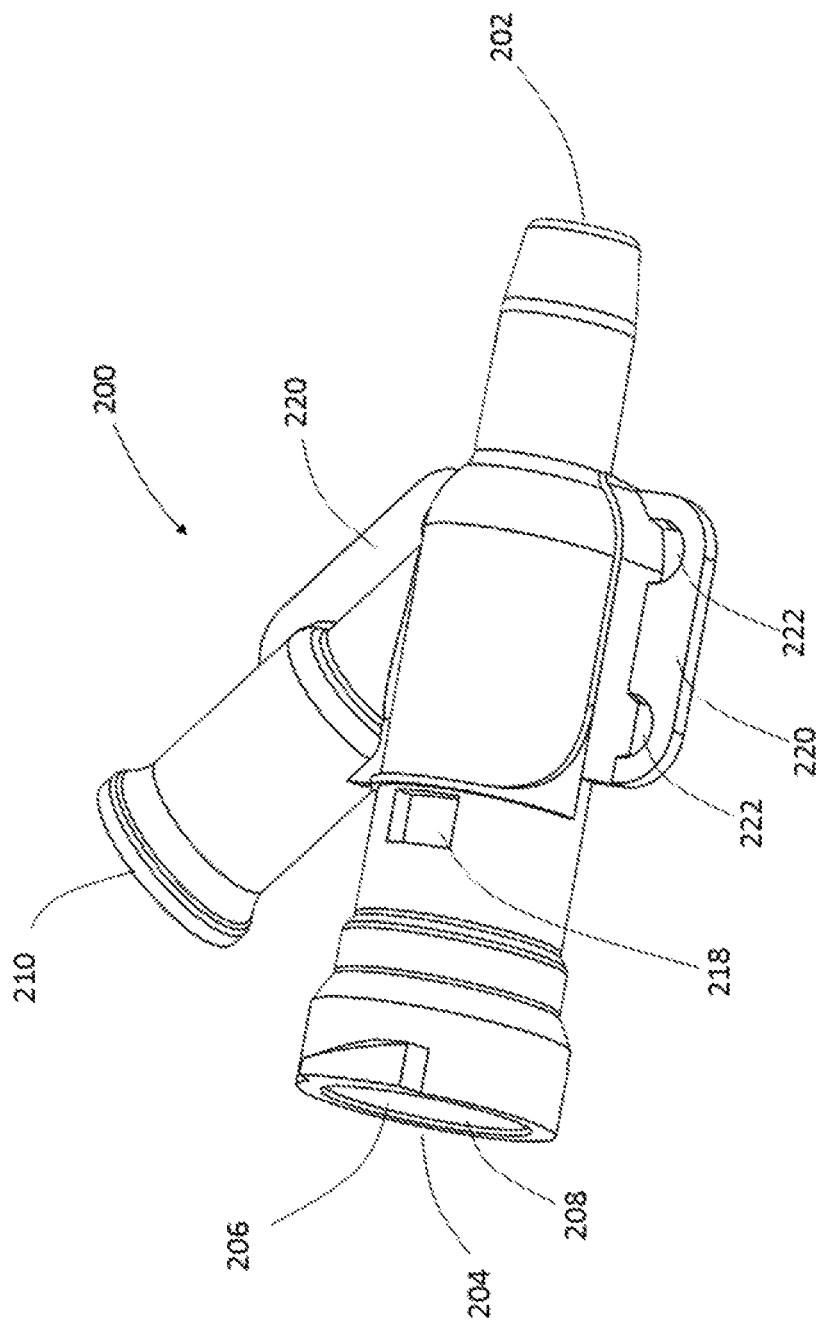
FIG. 2 is a perspective view depicting a catheter hub, in accordance with an embodiment of the disclosure.
Figure 6:
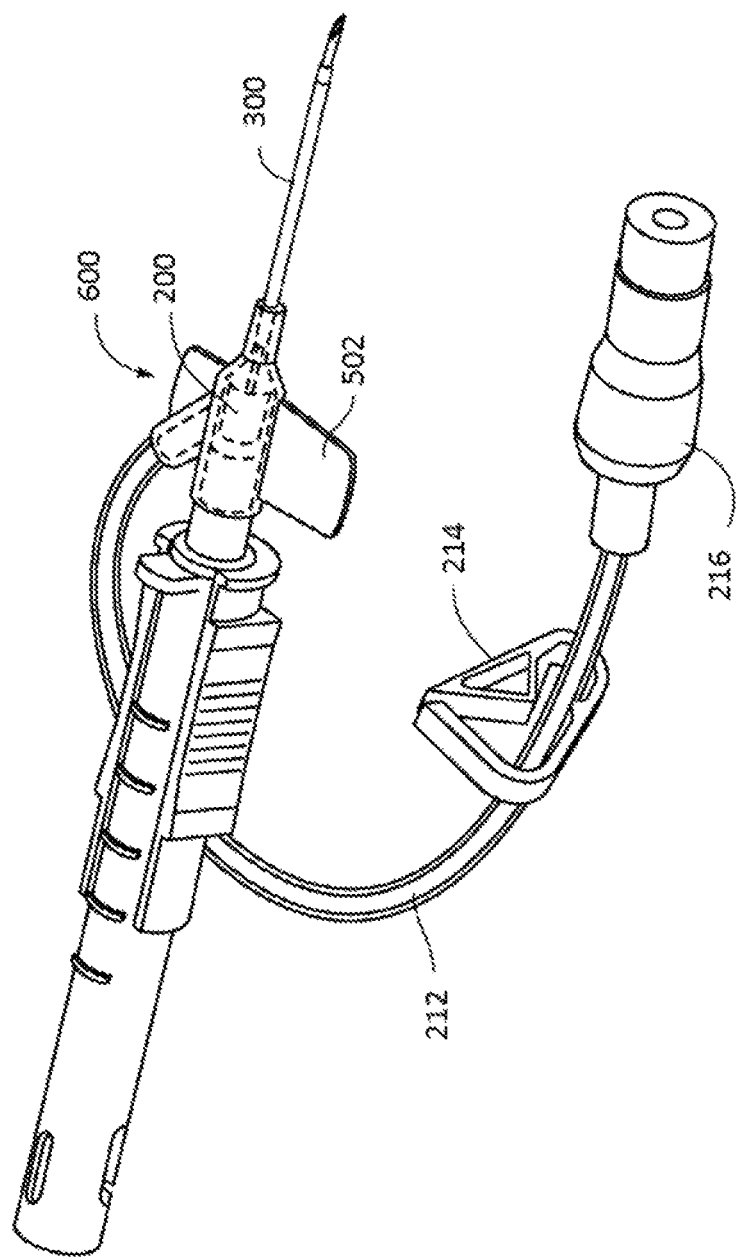
FIG. 6 is a perspective view of a catheter assembly operably coupled to a catheter insertion device, in accordance with an embodiment of the disclosure.

Referring to FIG. 1, a process 100 of constructing a catheter assembly as depicted in accordance with an embodiment of the disclosure. At 102, a catheter hub is molded. Referring to FIG. 2, an exemplary catheter hub 200 is depicted in accordance with an embodiment of the disclosure. The catheter hub 200 can have a distal end 202, a proximal end 204, and an internal wall 206 defining an internal fluid passageway 208 therebetween. In one embodiment, the proximal end 204 can define a threaded coupling, or the like, such as a Luer lock coupling, for operable coupling of the proximal end 204 of the catheter hub 200 to at least one of a catheter insertion device, IV fluid tubing, a blood or bodily fluid withdrawal device, and/or other medical device for monitoring a condition of a patient. In other embodiments, the proximal end 204 can be configured to operably couple to a needle insertion device (such as that depicted in FIG. 6), such that upon retraction of a needle of the needle insertion device, the proximal end 204 is thereafter sealed.

In one embodiment, the internal fluid passageway 208 can define a side port 210 in communication with the internal fluid passageway 208. In some embodiments, a length of hollow tubing 212 (depicted in FIG. 6) can be operably coupled to the side port 210. The hollow tubing 212 can be substantially transparent or translucent to enable observation of fluid within the hollow tubing 212. In one embodiment, the hollow tubing 212 can further include a tubing clamp 214 and a tube connector 216. In one embodiment, the tube connector can be constructed of a resilient material that can be deformed to selectively occlude hollow tubing 212 to inhibit the passage of fluid therethrough.

In one embodiment, the internal fluid passageway 208 can define an injection mold window 218 located between the distal end 202 and the proximal end 204. The injection mold window 218 can be appropriately sized and shaped to enable the flow of injection molded material under pressure into the internal fluid passageway 208 of the mold catheter hub 200. For example, in one embodiment, the injection mold window 218 can be rectangular in shape, and can be positioned between the proximal end 204 of the catheter hub and the side port 218 defined by the internal wall 206.

In one embodiment, the catheter hub 200 can further include one or more ledges 220 configured to provide structural reinforcement as support for a wing assembly. In one embodiment, the ledges 220 can define one or more holes 222. The holes 222 can provide improved contact with the wing assembly, when the wing assembly is integrally molded onto a portion of the catheter hub 200. Accordingly, the ledges 220 can serve to both increase the bonding surface between the catheter hub 200 and the wing assembly, as well as to serve as a partial structural reinforcement for the wing assembly, while at the same time enabling the assembly to maintain its flexibility.

With continued reference to FIG. 1, at 104, a catheter tube is seated into the molded catheter hub. Referring to FIGS. 3A-B, use of a catheter tube 300 seated in a catheter hub 200 are depicted in accordance with an embodiment of the disclosure. In one embodiment, the catheter hub can have a distal end 302, a proximal end 304, and a catheter wall 306 defining a lumen 308 in fluid communication with the internal fluid passageway 208 of the catheter hub 200. In seating of the catheter tube 300 to the catheter hub 200, the distal end 302 of the catheter tube 300 can be threaded through the proximal end 204 of the catheter hub 200, and pushed distally through the internal fluid passageway 208 until a portion of the catheter tube 300 in proximity to the proximal end 304 of the catheter tube makes abutting contact with a corresponding portion of the catheter hub and proximity to the distal end 202 of the catheter hub 200. In one embodiment, the seating of the catheter tube 300 within the catheter hub 200 can be performed via a seating machine, separate from the tool utilized to mold the catheter hub 200. Thereafter, the catheter tube 300 can be held in position relative to the catheter hub 200 via a friction fitting. Alternatively, an adhesive, ultrasonic welding, or the like can be utilized as an aid in retaining the catheter tube 300 relative to the catheter hub 200.

Figure 4:
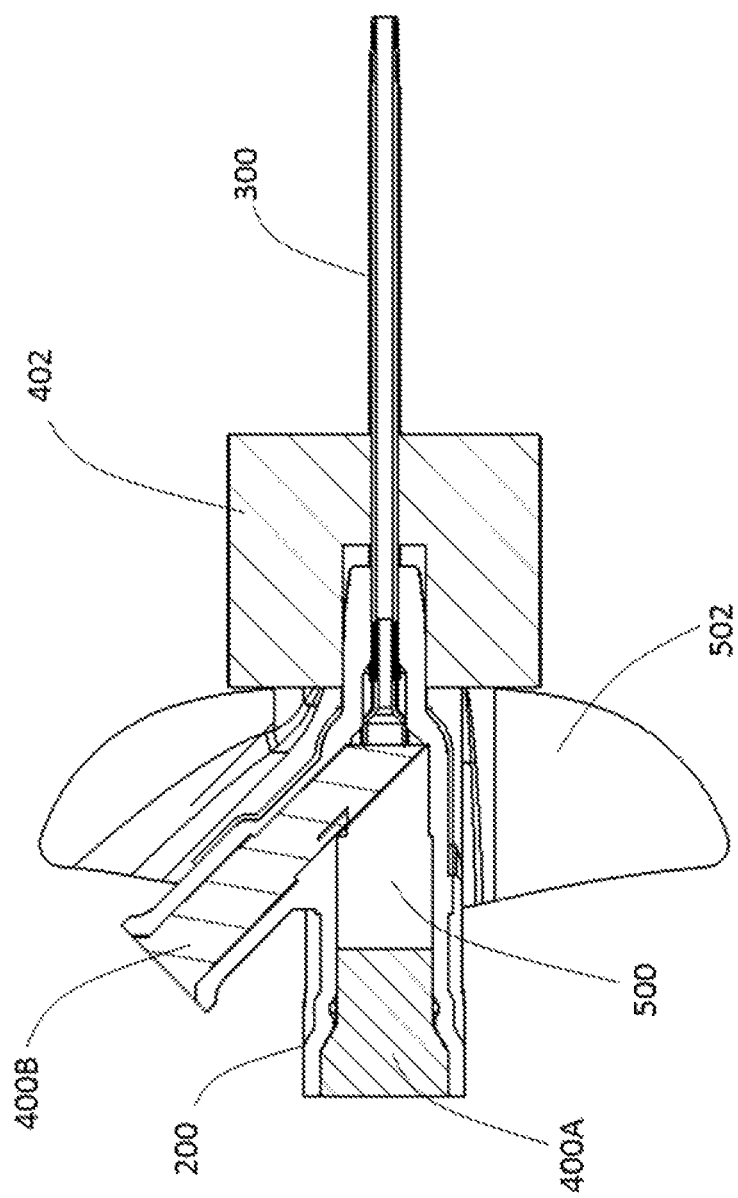
FIG. 4 is a cross-sectional view depicting a catheter hub and catheter tube with certain portions of internal fluid passageways therethrough plugged in preparation for injection molding, in accordance with an embodiment of the disclosure.

With continued reference to FIG. 1, at 106, portions of the internal fluid passageway 208 extending to the exterior of the catheter hub 200 can be plugged in anticipation of molding the septum. Referring to FIG. 4, the positioning of a molding core shut off pin 400 within the catheter hub 200 and catheter tube 300 assembly is depicted in accordance with an embodiment of the disclosure. In one embodiment, this can include a proximal end catheter hub molding core shut off pin 400A and a side port molding core shut off pin 400B. The proximal and catheter hub molding core shut off pin 400A can be configured to make sealing contact with the internal wall 206 of the catheter hub. The side port molding core shut off pin 400B can be configured to make sealing contact with the internal wall 206 of the catheter hub 200, as well as optionally the proximal end 304 of the catheter tube 300, thereby adding an extra layer of protection to inhibit injected material from entering the catheter tube 300. In one embodiment, a bushing 402 can be positioned over at least a portion of the catheter hub 200 to inhibit injection molded material from entering that portion of the assembly.

With continued reference to FIG. 1, at 108, a quantity of injection molded material can be injected through the injection mold window 218 of the catheter hub 202, thereby filling a portion of the internal fluid passageway 208. In one embodiment, the injection molded material fills the internal fluid passageway between the proximal and catheter hub molding core shut off pin 400A and the side port molding core shut off pin 400B, thereby forming a septum 500. In one embodiment, at least a portion of the septum 500 can extend through the injection mold window 218, thereby aiding in the retention of the septum 500 within the internal fluid passageway 208 upon removal of the proximal end catheter hub molding core shut off pin 400A and a side port molding core shut off pin 400B. In one embodiment, the molding core shut off pins 400A-B can be configured to enable the septum 500 formed within the catheter hub 200 to be shaped and sized to reduce voids or pockets within an internal fluid passageway of the catheter hub where slower moving fluid flowing therethrough may tend to stagnate.

In one embodiment, catheter hub wings 502 can be overmolded onto at least a portion of the catheter hub 200 concurrently with the molding of the septum 500. In particular, the catheter hub wings 502 can be overmolded over the one or more ledges 220 of the catheter hub, such that the overmolded catheter hub wing material flows into the one or more holes 222 defined within the one or more ledges 220.

Referring to FIGS. 5A-B, an assembled catheter assembly 600 is depicted in accordance with an embodiment of the disclosure. Construction of the catheter assembly 600 in which the catheter hub wings 502 are formed concurrently with, and of the same material as, the septum 500 enables the construction of a catheter assembly 600 with fewer parts, and results in a more robust structure, as the various components are integrally formed together and/or interconnected. As a result, the catheter assembly 600 can be formed with three components: a catheter hub 200, a catheter tube 300, and an integrated septum 500/wing assembly 502. Thereafter, disassembly of the three components would generally require destruction of the catheter assembly 600.

Moreover, as the septum 500 is injection molded into the catheter hub 200 and the disclosed process 100, the assembly step of inserting a separate, stand-alone septum into a catheter hub common to conventional assembly processes can be eliminated. Accordingly, embodiments of the present disclosure result in a faster and more streamlined assembly process, as well as a more robust catheter assembly 600.

With continued reference to FIG. 1, at 110, a slit 504 or pierce can optionally be defined in the septum 500. Defining such a slit 504 or pierce in the septum 500 can reduce the frictional force required to insert and/or withdraw a needle through the septum 500. Various slits and/or pierces, such as a single slit, tri-slit, and combination slit and pierce are contemplated.

At 112, a proximal hub component 224 can be optionally added to the proximal end 204 of the catheter hub 200, thereby axially compressing the molded septum 500. Axial compression of the molded septum 500 can aid in inhibiting bodily fluid from flowing through the slit 504 or pierce defined within the septum 500. In some embodiments, the proximal hub component 224 can further be configured to mate with a needle insertion device (such as that depicted in FIG. 6).

Figure 7:
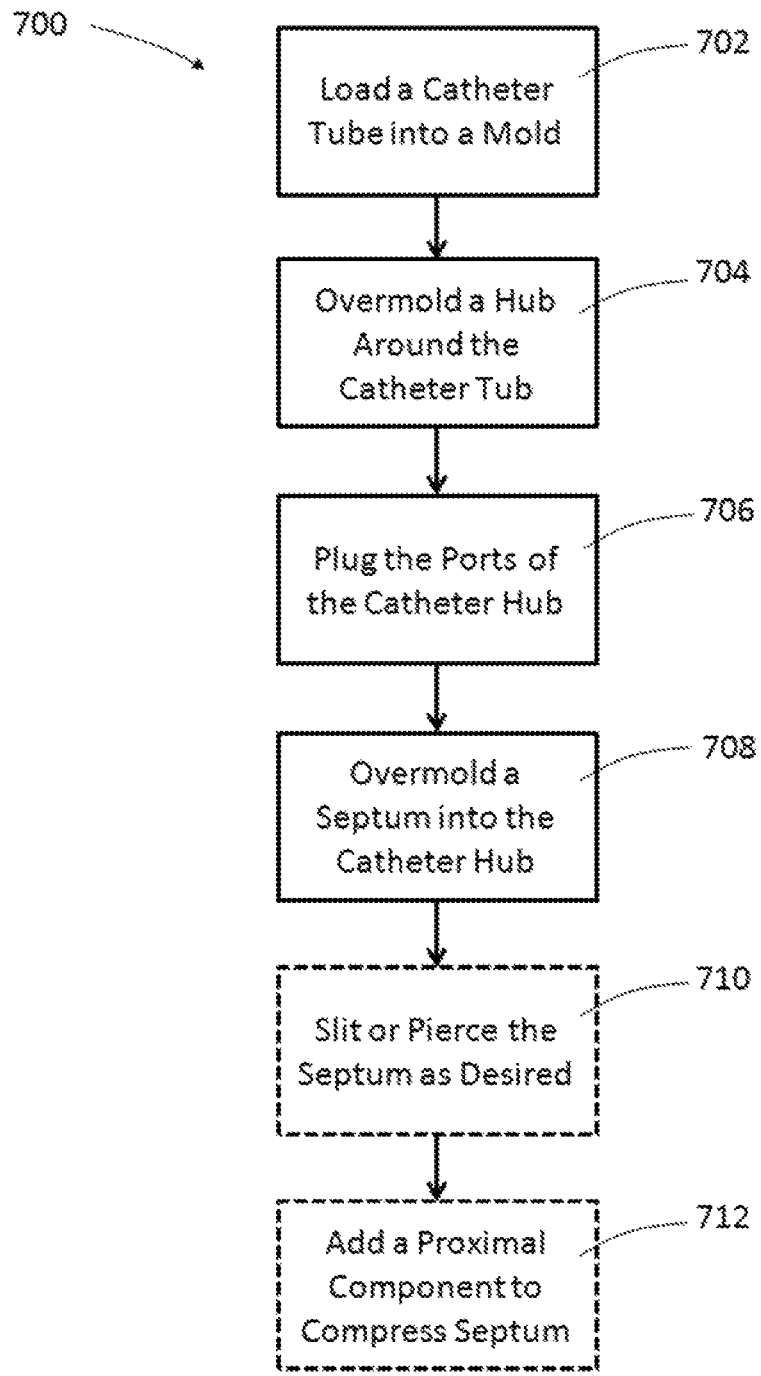
FIG. 7 is a flowchart depicting an alternative process of constructing a catheter assembly, in accordance with an embodiment of the disclosure.

Referring to FIG. 7, an alternative process 700 of constructing a catheter assembly 600 is depicted in accordance with an embodiment of the disclosure. According to process 700, the various process steps can be completed by a single injection molding apparatus, without having to move the partially constructed catheter assembly. In one embodiment of the process 700, at 702, a catheter tube 300 is loaded into a mold for the injection molding of a catheter hub 200. At 704, the catheter hub 200 is overmolded around the catheter tube 300, thereby fixedly coupling at least the proximal end 304 of the catheter tube 300 within the distal end 202 of the catheter hub 200. Like process 100, the catheter hub 200 can include an injection mold window 218.

At 706, portions of the internal fluid passageway 208 extending to the exterior of the catheter hub 200 can be plugged in anticipation of molding the septum. Like process 100, this can optionally include a proximal end catheter hub molding core shut off pin 400A, a side port molding core shut off pin 400B, and a bushing 402 positioned over at least a portion of the catheter hub 200 to inhibit injection molded material from entering those portions of the assembly. At 708, a quantity of injection molded material can be injected through the injection mold window 218 of the catheter hub 202, thereby filling a portion of the internal fluid passageway 208 to form the septum 500. In one embodiment, catheter hub wings 502 can be overmolded onto at least a portion of the catheter hub 200 concurrently with the molding of the septum 500.

At 710, a slit 504 or pierce can optionally be defined in the septum 500. At 712, a proximal hub component 224 can be optionally added to the proximal end 204 of the catheter hub 200, thereby axially compressing the molded septum 500.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

It is also to be appreciated that the term "distal," as used herein, refers to the direction along an axis that lies parallel to a needle cannula of a safety catheter assembly that is closest to the subject during catheter insertion. Conversely, the term "proximal," as used herein, refers to the direction lying along the axis parallel to the needle cannula that is further away from the subject when the catheter is inserted into the vein of the subject, opposite to the distal direction.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A method of constructing a catheter assembly, comprising:
    molding a catheter hub having a distal end, a proximal end, and an internal wall defining an internal fluid passageway therebetween, the internal wall defining an injection mold window located between the distal end and the proximal end;
    seating a catheter tube within the internal fluid passageway of the catheter hub, such that a proximal end of the catheter tube resides within the internal fluid passageway of the catheter hub, and a distal end of the catheter tube extends distally from the distal end of the catheter hub;
    plugging the proximal end of the catheter hub with a first mold core shut off pin and plugging a portion of the internal fluid passageway in proximity to the proximal end of the catheter tube with a second mold core shut off pin; and
    injection molding a septum in between the first mold core shut off pin and the second mold core shut off pin through the injection mold window.

2. The method of claim 1, further comprising defining a slit and/or pierce in the septum.

3. The method of claim 1, further comprising adding a proximal hub component to the proximal end of the catheter hub to compress to the septum.

4. The method of claim 1, further comprising overmolding material around at least a portion of the catheter hub concurrently with the molding of the septum.

5. The method of claim 4, wherein the overmolded material includes wings.

6. The method of claim 1, wherein the internal wall of the catheter hub further defines a side port in communication with the internal fluid passageway.

7. The method of claim 6, further comprising operably coupling a length of tubing to the side port.

8. The method of claim 1, wherein the septum extends at least partially through the injection mold window, thereby aiding in the retention of the septum within the internal fluid passageway.

9. A method of constructing a catheter assembly, comprising:
    loading a catheter tube having a proximal end and a distal end into a catheter assembly mold;
    overmolding a catheter hub around at least the proximal end of the catheter tube, the catheter hub having a distal end, a proximal end, and an internal wall defining an internal fluid passageway therebetween, the internal wall defining an injection mold window located between the distal end and the proximal end;

plugging at least the proximal end of the catheter hub with a mold core shut off pin; and injection molding a septum in at least a portion of the internal fluid passageway between the mold core shut off pin and the proximal end of the catheter tube through the injection mold window, the septum defining a beveled distal end configured to reduce a pocket within the internal fluid passageway to inhibit stagnation of fluid flowing therethrough.

10. The method of claim 9, further comprising defining a slit and/or pierce in the septum.

11. The method of claim 9, further comprising adding a proximal hub component to the proximal end of the catheter hub to axially compress to the septum.

12. The method of claim 9, further comprising overmolding wings around at least a portion of the catheter hub concurrently with the molding of the septum.

13. The method of claim 9, wherein the internal wall of the catheter hub further defines a side port in communication with the internal fluid passageway.

14. The method of claim 13, further comprising operably coupling a length of tubing to the side port.

15. The method of claim 9, wherein the septum extends at least partially through the injection mold window, thereby aiding in the retention of the septum within the internal fluid passageway.

* * * * *